United States Patent [19]

Weiss et al.

[11] Patent Number: 5,469,751

[45] Date of Patent: Nov. 28, 1995

[54] MANIFOLDED SAMPLING VALVE ASSEMBLY

[75] Inventors: Bruce W. Weiss, Whitefish Bay; Eugene R. Rommelfaenger, Neosho, both of Wis.

[73] Assignee: Sentry Equipment Corp., Oconomowoc, Wis.

[21] Appl. No.: 248,662

[22] Filed: May 25, 1994

[51] Int. Cl.⁶ .......................... F16K 11/22; G01N 1/10
[52] U.S. Cl. .................... 73/863.33; 73/863.86; 137/625.4; 137/606
[58] Field of Search ............... 73/863.33, 863.86, 73/863.71, 863.72, 863.73, 864.83, 864.84; 137/625.4, 625.41, 606, 607, 897, 898, 625.65, 625.66, 628, 634.16; 251/129.11

[56] References Cited

U.S. PATENT DOCUMENTS

| | | | |
|---|---|---|---|
| 2,267,515 | 12/1941 | Wilcox et al. | 137/139 |
| 2,634,743 | 4/1953 | Audemar | 137/606 X |
| 2,799,293 | 6/1957 | Clay | 137/620 |
| 2,920,651 | 1/1960 | Welsh | 137/625.4 X |
| 2,977,989 | 4/1961 | Meynell | 137/630.19 |
| 3,036,229 | 5/1962 | Kemp et al. | 307/115 |
| 3,043,145 | 6/1962 | Hoffman . | |
| 3,357,232 | 12/1967 | Lauer . | |
| 3,369,405 | 2/1968 | Galegor | 73/863.33 X |
| 3,596,678 | 8/1971 | Kutrubs et al. | 137/607 X |
| 3,608,587 | 9/1971 | Zbell | 137/625.66 |
| 3,738,388 | 6/1973 | Parker et al. | 137/607 X |
| 3,747,623 | 7/1973 | Greenwood et al. | 137/269 |
| 3,757,583 | 9/1973 | Ludewig, Jr. | 73/863.33 |
| 3,827,302 | 8/1974 | Sato | 73/863.33 |
| 4,051,862 | 10/1977 | Haytayan | 137/454.2 |
| 4,458,543 | 7/1984 | Mieth | 73/863.86 |
| 4,529,006 | 7/1985 | Block et al. | 137/625.65 |
| 4,584,888 | 4/1986 | Bradley | 73/863.33 X |
| 4,611,631 | 9/1986 | Kosugi et al. | 137/625.65 |
| 4,664,150 | 5/1987 | Steiger | 137/625.27 |
| 4,764,758 | 8/1988 | Skala | 73/863.01 X |
| 4,800,308 | 1/1989 | Tice | 310/83 |
| 4,848,387 | 7/1989 | Hon | 137/592 X |
| 4,993,271 | 2/1991 | Vargason | 73/863.33 X |
| 5,137,257 | 8/1992 | Tice | 251/129.11 |
| 5,259,416 | 11/1993 | Kunz et al. | 137/883 |

FOREIGN PATENT DOCUMENTS 85352  5/1985  Japan .................... 73/863.33

OTHER PUBLICATIONS

"Programmable gas sample collector"; Kent Tech Rev. (GB) No. 25 Jul. 1979 pp. 12–13 in 73/863.33 by Andrew Benton of George Kent Electronic Products Limited.

*Primary Examiner*—Thomas P. Noland
*Attorney, Agent, or Firm*—Jansson & Shupe, Ltd.

[57] ABSTRACT

The improved valve assembly controls flow of fluid in "stream sampling" applications. The assembly valve block has at least two inlet passages, an outlet passage and a separate flow control valve for connecting each inlet passage to the outlet passage. Each valve has a single primary valving surface and each of the two inlet passages is selectively placed in flow communication with the outlet passage by positioning one of the primary valving surfaces. Actuation of each valve places the corresponding inlet passage in flow communication with an outlet passage common to all inlet passages. Both ends of the outlet passage are connected together by a "smooth bend" curvilinear tube attached to a fluid analyzer. The assembly can be operated by a control device for "programmed" stream sampling.

17 Claims, 6 Drawing Sheets

# MANIFOLDED SAMPLING VALVE ASSEMBLY

FIELD OF THE INVENTION

This invention relates generally to fluid handling and, more particularly, to analysis of samples of fluid drawn from process flow lines as found in, for example, electrical power generating and petrochemical manufacturing plants.

BACKGROUND OF THE INVENTION

"Process sampling" (as it is often referred to) is widely used for analyzing characteristics of liquids present in particular flow lines of process equipment. For example, the manufacturer of a pharmaceutical compound may want to test a characteristic of such compound (or of an ingredient thereof) for purity or concentration.

As other examples, water is used in power generation and in the manufacture of electronic products. Those who are carrying out such processes often wish to measure the presence of, e.g., silica, sodium and/or dissolved oxygen in the water or measure water turbidity.

For most applications, process sampling is carried out while the process is ongoing and while fluid is actually moving in the fluid flow line. And it is often desirable to draw samples of a particular fluid from several different locations in the process equipment. A common way of doing so is to mount a sampling nozzle at each such location (and such locations may be quite far apart from one another) and pipe fluid from the nozzles to a centralized sampling and analysis location where the sampling valves are located. Such valves are operated in some sort of coherent sequence.

The fluid samples drawn from such sampling valves are directed to a fluid analyzer. Such an analyzer is a device configured to provide information about one or more sample parameters, e.g., pH or dissolved oxygen content. Because fluid analyzers are relatively expensive, the practice is to use a single analyzer to provide information about fluid taken from each of several different locations in process equipment. Since samples are taken from any particular location at periodic intervals (rather than continuously), samples are taken from several locations in sequence and are routed to the analyzer in the same sequence.

A control device is often used to operate the several sampling valves. Such device, a programmable logic controller, a timer relay, a computer or the like, may be "programmed" to operate each of several sampling valves according to some coherent sampling strategy, often involving some sort of sequential valve operation.

While arrangements like those described above are generally satisfactory for their intended purpose, they tend to be characterized by certain disadvantages. One disadvantage is that mounting an individual sampling valve at each of several sampling locations is cumbersome and expensive in both labor and material. And if a single analyzer is used for several widely-spaced sampling valves, the volume of the "dead" fluid between a sampling valve outlet port and the analyzer may be very substantial. (Of course, the analyzer cannot be mounted adjacent to all of the separate, widely-spaced valves.) Dead fluid volume is an important concern and can have a direct bearing on the accuracy with which the analyzer provides information about the sample.

These factors suggest the use of a multi-port valve and, in fact, one type of multi-port fluid sampling valve is shown in technical literature titled "Whitey 'T2' Series Valves" and bearing the name "Swagelok Co." However, configurations of the depicted valve appear to have certain deficiencies. One is that it relies upon one or more O-rings for sealing at critical locations such as between the inlet and outlet ports. And other O-rings are used as sliding seals. It is thought that O-rings can prove unreliable, particularly in the presence of fluid contaminants and/or when used as dynamic seals.

Another apparent deficiency is that the inlet and outlet ports and passages are arranged so that inlet pressure is in a direction tending to lift the O-ring sealing between the inlet and outlet ports. Sealing is solely by spring pressure which must be sufficiently high to overcome this "liftoff" tendency and assure a good seal.

The apparent need for high spring force probably accounts for the fact that the Whitey valves are pneumatically operated. It seems at least possible that spring pressure must be so high that a pneumatic actuator is required to operate the valve. Compressed air or other compressed gas is not often available at sampling locations or, if provided, is expensive to install. And, often, a device known as an "I-to-P" valve is needed and the current cost of such a valve is on the order of $100 each. (The I-to-P valve derives its name from the fact that it converts an electrical current signal, I, into a pressure signal, P.)

Other valves are shown in the patent literature. For example, U.S. Pat. No. 3,747,623 (Greenwood et al.) depicts a fluid flow control manifold with solenoid operated valves. Such manifold uses what are shown as looped tubes, one each for inlet and exhaust. Each valve has a pair of inlet ports connected together and a pair of outlet ports connected together. The solenoid controls two valves in tandem, one of which closes when the other opens.

That is to say, no valve is capable of operation by itself and no valve is capable of porting flow from a single inlet port to an outlet port. And the external tubing includes 90° bends which may contribute to fluid "dead legs" and, at the least, contributes to pressure drop along the tubing. Thus, neither the valves nor the manifold are suitable for sampling from individual lines.

U.S. Pat. No. 5,259,416 (Kunz et al.) depicts individually operable valves, each sealing against a flat-faced truncated-cone-shaped valve seat. The Kunz et al. valve has a common inlet and separate outlets. Actuation of either valve directs flow from the common inlet to only one of the outlets. Fluid flows from both outlets only if both valves are actuated.

U.S. Pat. No. 4,611,631 (Kosugi et al.) involves a poppet-type changeover valve with three passages and a closure member movable to seal against one or the other of two seats. While the patent does not so state, it appears from the arrangement of the closure member and the seats that port $2c$ is the inlet and ports $2b$ and $2d$ are outlet ports. The valve closure member shifts between two positions, either of which connects the assumed inlet to one of the assumed outlet ports. There is no opportunity to simultaneously flow fluid to both outlet ports.

U.S. Pat. No. 3,357,232 (Lauer) shows an analyzing apparatus which uses three ball-type, pneumatically-shifted shuttle valves to control flow. The user selects from one of two sample streams by introducing inert gas into port 5 or port 9. Either of two outlet pipes (e.g., pipes 11', 12'), are selected by introducing inert gas into port 14. But irrespective of the outlet pipe selected, all of the sampled fluid flows to a common gas analyzer. The legs 16, 21 do not carry fluid simultaneously and like the external tubing depicted in the Greenwood et al. patent, such legs have 90° bends.

An improved manifolded sampling valve which resolves some of the deficiencies of prior art valves would be an important advance in the art.

OBJECTS OF THE INVENTION

It is an object of the invention to provide an improved manifolded sampling valve assembly overcoming some of the problems and shortcomings of the prior art.

Another object of the invention is to provide an improved manifolded sampling valve assembly which maintains a continuous sample flow stream through such assembly.

Another object of the invention is to provide an improved manifolded sampling valve assembly which reduces the volume of "dead" fluid within such assembly and the volume of fluid in a common outlet passage.

Another object of the invention is to provide an improved manifolded sampling valve assembly in which wetted surfaces downstream of a valve are "swept" by flowing fluid whenever such valve is opened.

Another object of the invention is to provide an improved manifolded sampling valve assembly which reduces the volume of "dead" fluid between the valve assembly and an analyzer.

Yet another object of the invention is to provide an improved manifolded sampling valve assembly which is free of O-ring seals between the inlet and outlet ports.

Another object of the invention is to provide an improved manifolded sampling valve assembly which is free of pneumatic actuators.

Still another object of the invention is to provide an improved manifolded sampling valve assembly constructed so that inlet pressure tends to urge the valve sealing surface in a "valve-closed" direction.

Another object of the invention is to provide an improved manifolded sampling valve assembly having parallel-path exterior tubing free of sharp bends which may cause fluid "dead legs."

Yet another object of the invention is to provide an improved manifolded sampling valve assembly which maintains sampling flow velocities which helps prevent "settling" of fluid or fluid contaminants.

How these and other objects are accomplished will become more apparent from the following descriptions and from the drawing.

SUMMARY OF THE INVENTION

The invention is an improvement in a valve assembly for controlling flow of fluid and is particularly useful for periodic sampling of fluid streams of the type described above. The assembly has a valve block with at least two inlet passages, each connected to a different point in the equipment. The valve block also has an outlet passage connected to a fluid analyzer and a separate flow control valve for connecting each inlet passage to the outlet passage.

In the improvement, each valve has a primary valving surface and each of the two inlet passages is selectively placed in flow communication with the outlet passage by positioning the corresponding primary valving surface. The assembly includes provisions for parallel flow from the outlet passage to the analyzer.

Specifically, the outlet passage has first and second ends which are coupled in flow communication with one another by a curvilinear tube. A curvilinear tube is one having bends therein in which the bending radius (or radii) are several times greater than the diameter of the tube. The absence of sharp bends, e.g., 90° bends, and the provision of redundant, parallel flow paths for each inlet passage helps decrease pressure drop in the assembly and also helps prevent "dead legs," vagrant small quantities of accumulated fluid in the assembly.

The tube includes a connector about midway between the tube ends and such connector is in flow communication with a fluid analyzing device. In that way, the analyzing device is shared between (or among) the sample streams connected to the inlet passages and its available analytical time is more fully utilized.

In another aspect of the invention, the block of the new assembly includes at least two intermediate flow passages, e.g., first and second flow passages, each of which is in flow communication with the outlet passage. Each inlet flow passage and its corresponding intermediate flow passage can be selectively connected to the outlet passage (and thence to the analyzer) by operating the appropriate valve.

In a highly preferred embodiment, fluid flow in the first intermediate passage is in a first direction and fluid flow in the second intermediate passage is in a second direction. Preferably, such directions are about 180° from one another and the intermediate flow passages are coaxial. Further, the flow control valves are solenoid-actuated and the valves move in opposite directions when actuated. In that respect, the orientation of the valves to one another resembles a two-cylinder "flat opposed" internal combustion engine.

In another aspect of the invention, the assembly includes a separate drain passage for each inlet passage. Each such inlet passage contains pressurized fluid which is diverted to a drain passage when the valve is closed and which is routed to the outlet passage when the valve is open.

The primary valving surface abuts a valve face when the valve is closed and the pressurized fluid urges the valving surface toward the valve face when the valve is closed. This is a desirable feature since the greater the fluid pressure, the more tightly the valving surface is urged toward the valve face. Leakage is thus reduced or eliminated.

And the new valve assembly is not limited to individually sampling only two or four process streams. The new assembly conveniently facilitates "ganged" arrangements for sampling more than four process streams. In such an arrangement, there is a first valve block having two (most preferably, four) inlet passages and two (most preferably, four) intermediate flow passages. The assembly has plural flow control valves, each valve selectively placing a separate inlet passage in flow communication with a separate intermediate flow passage and thence with the outlet passage of that valve block.

The assembly also has a second valve block having its own, i.e., second, outlet passage. Each of the outlet passages in the first block and the second block has a first end and a second end. In ganged arrangement, the second end of the first outlet passage and the first end of the second outlet passage are connected together by tubing.

As in the first valve block, the second valve block has (a) two inlet passages, (b) two intermediate flow passages, and (c) a pair of flow control valves. Each valve selectively places a separate inlet passage in the second valve block in flow communication with a separate intermediate flow passage in the second valve block. In the two-block ganged arrangement, the first end of the first outlet passage and the second end of the second outlet passage are connected together by a curvilinear tube. In the manner of the "one-block" assembly, the curvilinear tube has ends and includes a connector in flow communication with a fluid analyzing device.

Further details of the invention are set forth in the following detailed description and in the drawing.

DETAILED DESCRIPTION OF PREFERRED EMBODIMENTS

Before describing details of the new manifolded sampling valve assembly 10, it will be helpful to gain a better appreciation of a way in which such assembly 10 may be used. In this specification, reference is made to liquid sampling but it is to be understood that the new assembly 10 may be adapted for gas sampling, as well.

Figure 1:
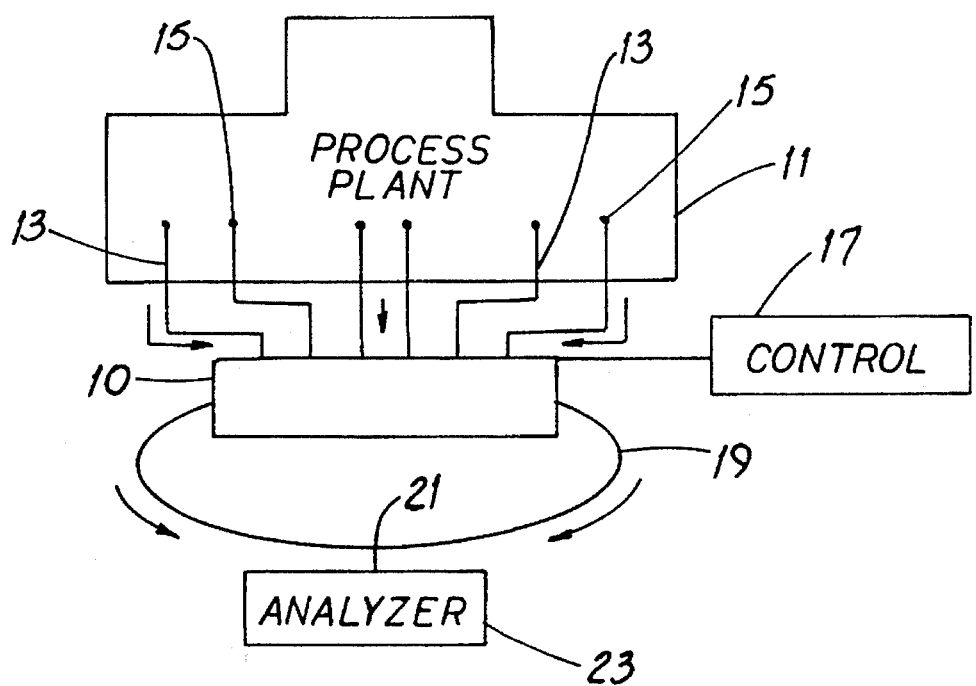
FIG. 1 is a representative view of how the new sampling valve assembly may be used to sample "streams" of liquid in a process plant.

Referring to FIG. 1, a process plant 11 (such as for generating power, manufacturing a petrochemical product or the like) has a number of liquid flow lines 13 from which samples of liquid are taken at various sampling points 15. Liquid samples flow along the lines 13 to the assembly 10.

A control device 17 (e.g., timer relay, programmable logic controller) operates the assembly 10 in a way that liquid from each of the lines 13 is directed in some usually-predetermined sequence to an externally-connected tube 19. In turn, the tube 19 has a connector 21 attached to an analyzer 23 through which the liquid flows. The analyzer 23 provides information about some characteristic, e.g., mineral content, turbidity or the like, of the liquid.

It is to be appreciated that it is desirable to perform "sample conditioning" before the sampled fluid is brought to the assembly 10. Such conditioning, as particularly espoused by Sentry Equipment Corp. of Oconomowoc, Wis., U.S.A., involves reducing fluid temperature and pressure and maintaining fluid flow rate before a sample is taken.

Figure 2:
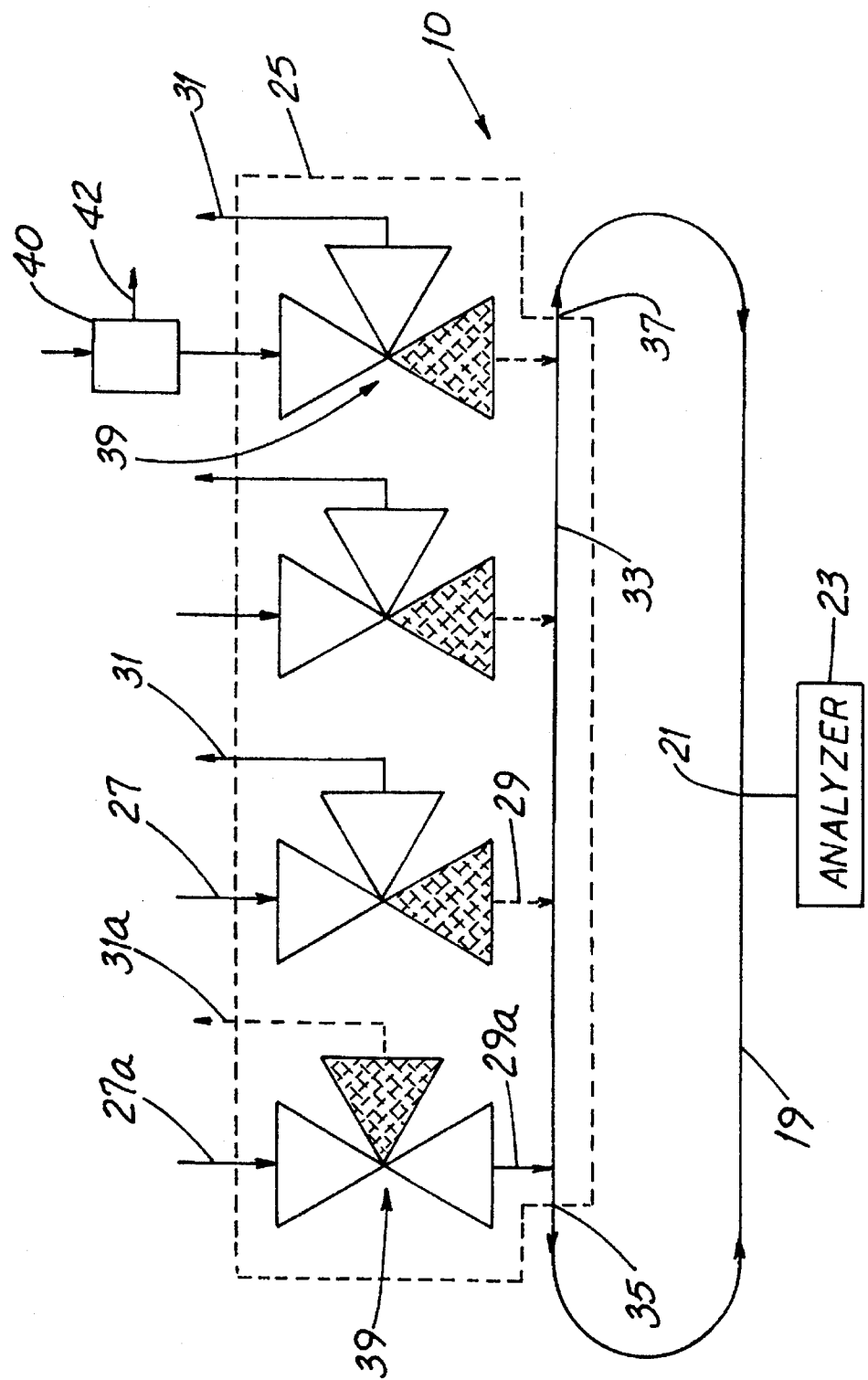
FIG. 2 is a schematic circuit diagram of the manifolded sampling valve assembly.

Referring now to FIG. 2, the circuit diagram for the new valve assembly 10 will be described by identifying symbolic portions thereof, e.g., ports, passages and the like, using the same numerals used to identify the corresponding aspects of the actual valve assembly 10 described in connection with other FIGURES. The assembly 10 has a valve block 25 in which is formed a plurality of separate inlet passages 27 and a plurality of intermediate flow passages 29. There is also a plurality of drain passages 31 and as described in more detail below, each inlet passage 27 functions in association with a particular flow passage 29 and a particular drain passage 31. For example, the inlet passage 27a functions only in association with the flow passage 29a and the drain passage 31a.

(It is to be appreciated that the term "drain" in the phrase "drain passage" does not necessarily imply that the fluid is discarded. The phrase "bypass passage" is equally apt for passages 31.)

The intermediate flow passages 29 are in flow communication with a common outlet passage 33 having a first end 35 and a second end 37. The ends 35, 37 are coupled in flow communication with one another by the curvilinear tube 19 having the connector 21 in flow communication with the analyzer 23.

The assembly 10 also has a plurality of two position solenoid-actuated valves 39. Each such valve 39 is used to direct liquid from a particular inlet passage 27 to either a particular intermediate flow passage 29 and thence to the outlet passage 33 or, when the valve 39 is de-energized, to a particular drain passage 31.

In FIG. 2, the lefthand valve 39 is energized and open so that liquid flows from the inlet passage 27a through the passage 29a to the common outlet passage 33 and thence to the analyzer 23. The drain passage 31a is blocked. In use, only a single valve 39 is open at a particular time.

In the field of sampling valves, much has been made of "double-block-and-bleed" valves, i.e., valves which have a bypass line (the "bleed") and two redundant valve closures in series between an inlet passage and the valve per se. Any of the valves 39 in the assembly 10 can be configured as a double-block-and-bleed valve by adding a three-way valve 40 ahead of an inlet passage 27.

The valve 40 is preferably solenoid operated and in one position permits fluid to flow to passage 27 and blocks drain passage 42. In the other position, passage 27 is blocked and fluid flows to passage 42 which may be "teed" to passage 31.

Figure 3:
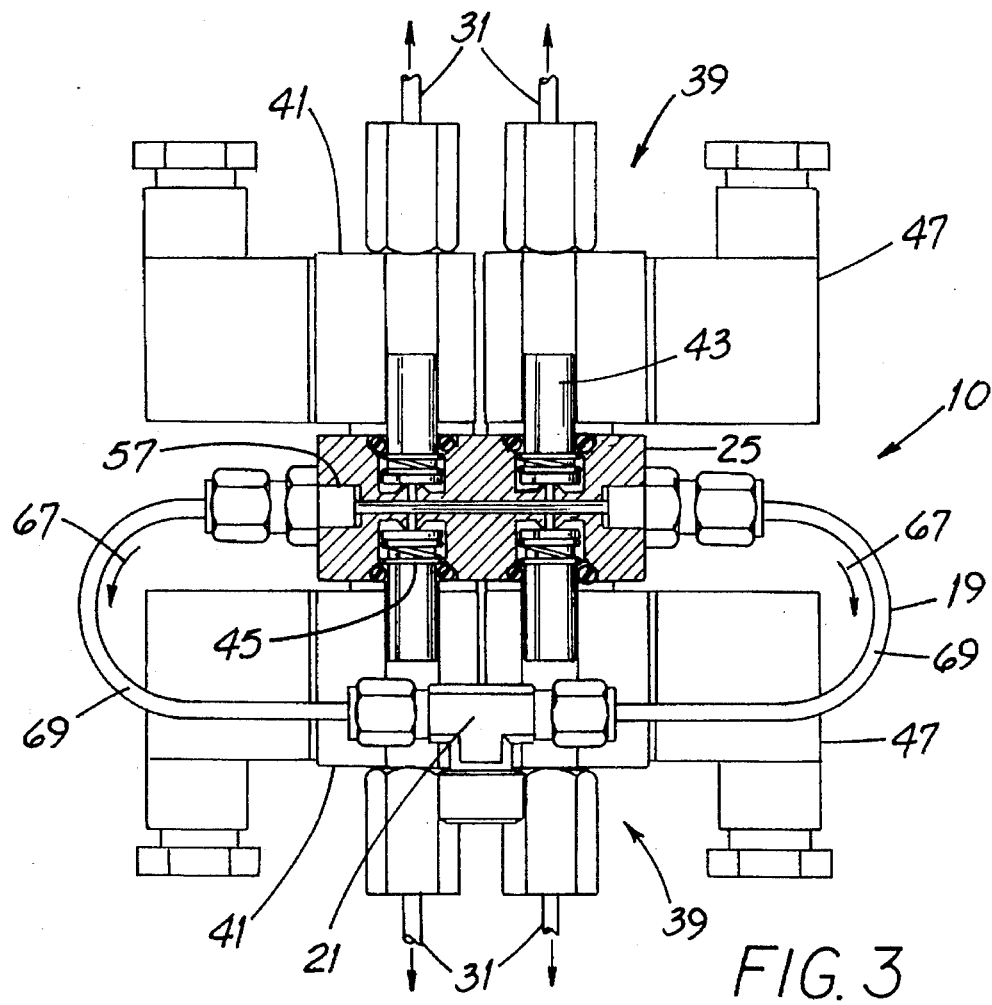
FIG. 3 is a front elevation view of the valve assembly. Parts are shown in cross-section and other parts are broken away.
Figure 5:
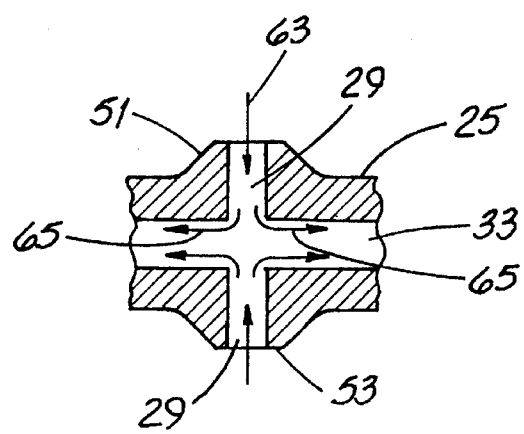
FIG. 5 is a cross-section elevation view of a portion of the valve block used in the assembly. Parts are broken away.
Figure 4:
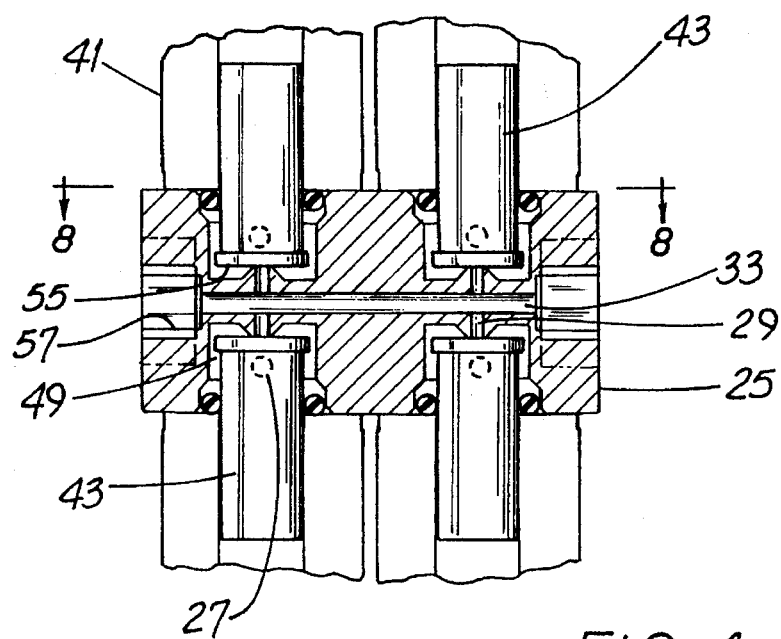
FIG. 4 is an elevation view, somewhat enlarged, of a portion of the valve assembly of FIG. 3. Parts are shown in cross-section, surfaces of parts are shown in dashed outline and other parts are omitted for clarity.

Referring now to FIGS. 3, 4 and 5, the assembly 10 includes the valve block 25 (shown in cross-section) into which is fitted plural solenoid-actuated valves 39. Each valve 39 has a coil housing 41 and a solenoid plunger 43 which moves away from the block 25 when the associated coil is energized.

When the coil is de-energized, the plunger 43 is urged toward the block 25 by a compression spring 45 and by the fact that the pressure in the inlet passage 27 is greater than that in the intermediate flow passages 29. To put it another way, the pressure "drop" across the plunger 43 is in a direction to urge such plunger 43 toward the block 25 to more tightly seal the passage 29. Connection boxes 47 are provided to connect electrical wiring to the coils.

The block 25 has plural inlet passages 27 and in the depiction of FIG. 4, such passages 27 extend in a direction perpendicular to the plane of the drawing sheet. Each such passage 27 communicates with a separate annular cavity 49 in the block 25 and in the depiction of FIG. 4, the passage 27 opens into the cavity 49 at a location behind the solenoid valve plunger 43. Thus, the passages 27 are shown in dashed outline.

Figure 6:
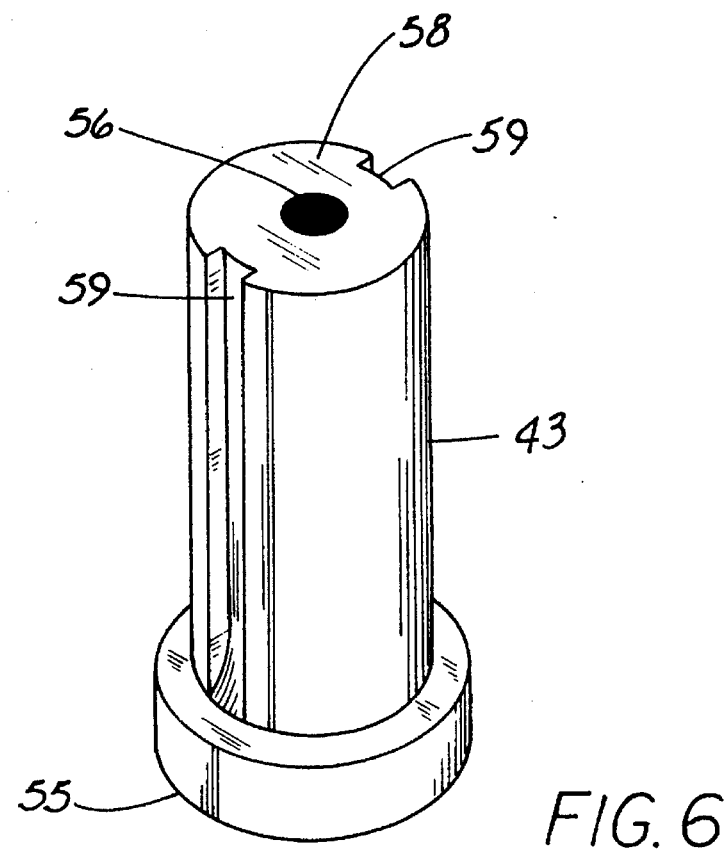
FIG. 6 is an isometric view, greatly enlarged, of a solenoid valve plunger of the type used in the valve assembly.

Referring to FIGS. 4 and 6, each of a plurality of intermediate flow passages 29 (four in the depicted block 25; one such passage 29 corresponding to each inlet passage 27) is in continuous flow communication with an outlet passage 33 described in more detail below. It is to be appreciated that these passages 29 shown in FIG. 5 and to the left in FIG. 4 are coaxial with one another and that fluid flowing in such passages 29 flows toward the outlet passage 33. That is, such fluid flow is in two directions about 180° from one another. The two opposed passages 29 to the right in FIG. 4 are similarly arranged and fluid flows through them in the same way.

The intermediate flow passages 29 are extremely short, have very small contained volume and are formed in truncated-cone-shaped "bosses" 51. Each boss 51 has a smooth, substantially flat valve face 53. When a solenoid coil is de-energized, an elastomer disk on the primary valving surface 55 of the plunger 43 contacts the face 53 and prevents fluid from flowing through that intermediate flow passage 29. Conversely, when a coil is energized, its plunger surface 55 is spaced from the corresponding face 53 and fluid can flow through that corresponding passage 29.

The valve block 25 has an outlet passage 33 which extends the length of the block 25 and is terminated at the first (left) and second (right) passage ends 35 and 37, respectively, by threaded ports 57. The ends 35, 37 are coupled in flow communication with one another by the curvilinear tube 19. Such tube 19 is free of "angle-like" bends, i.e., bends such as would be defined by two straight lengths of tube intersecting at an angle. The tube has a "T" connector 21 about midway between the ends 35, 37 and the connector 21 is attached to the fluid analyzer 23.

There are also plural drain passages 31, one for each inlet passage 27 and each cavity 49. In the depictions of FIGS. 3 and 4, the drain passages 31 for the two upper cavities 49 extend upward while those for the two lower cavities 49 extend downward. As shown in FIG. 6, the solenoid plunger 43 includes a pair of longitudinal grooves 59 which communicate between a particular cavity 49 and the drain passage 31 associated with such cavity 49. When a solenoid coil is deenergized and its plunger 43 abuts the associated valve face 53, fluid flowing in the inlet passage 27 flows along the grooves 59 and to and through the drain passage 31. When the coil is energized, the drain passage 31 is closed by an elastomer disc 56 at the top of the plunger 43. Such disc 56 defines a secondary valving surface 58. With the drain passage 31 closed, fluid is forced to flow to an intermediate flow passage 29 and thence to the outlet passage 33.

From the foregoing and from an inspection of FIGS. 3 and 5, it is to be appreciated that any fluid flowing in any intermediate passage (as symbolized by the arrow 63) flows through the outlet passage 33 in two opposite directions as symbolized by the arrows 65. Both directions are away from that particular intermediate passage 29. It is also to be appreciated that as symbolized by the arrows 67, such fluid flows to the connector 21 along both legs 69 of the tube 19. Thus, there are parallel flow paths between each intermediate passage 29 and the connector 21.

Figure 7:
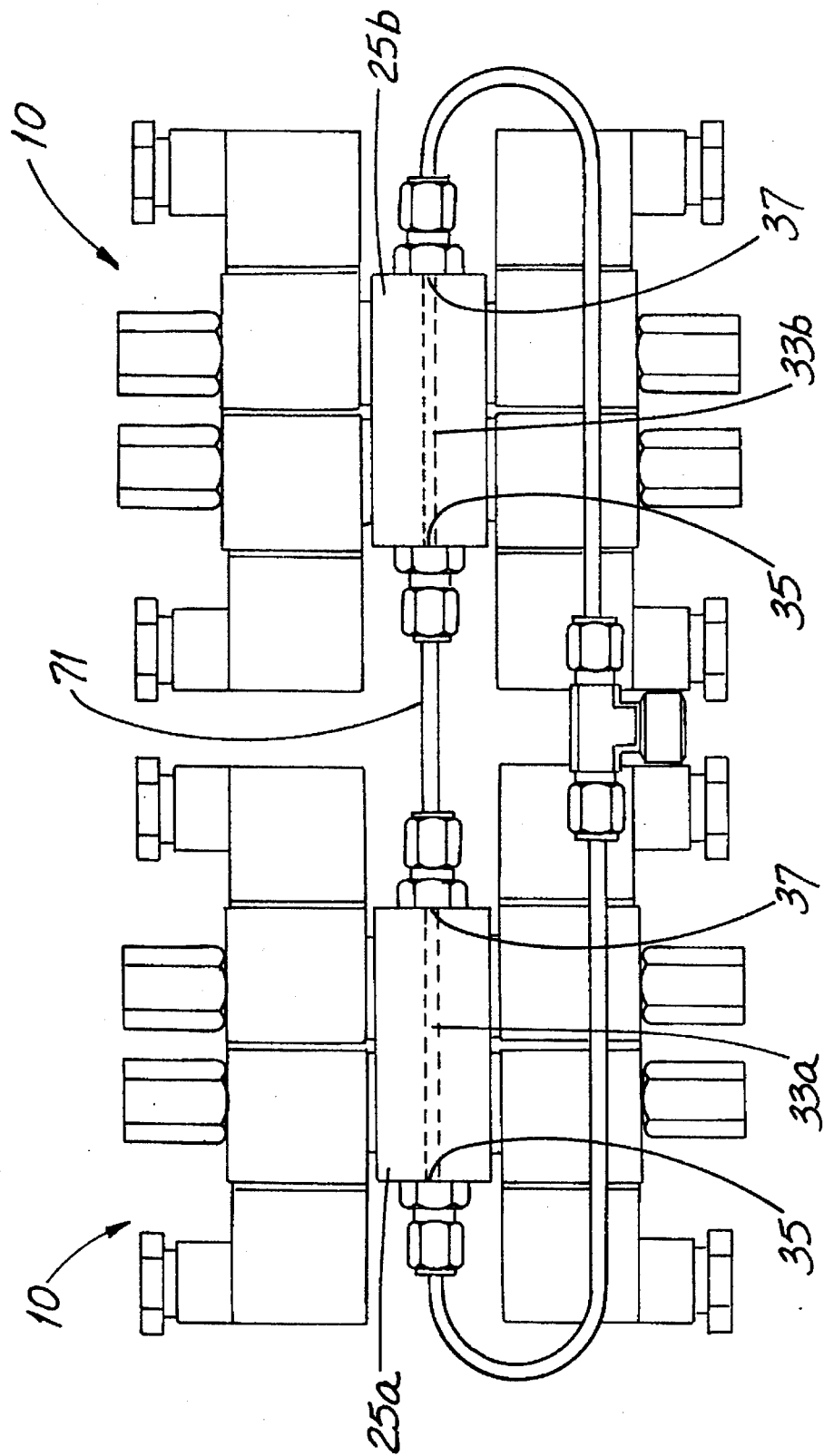
FIG. 7 is a front elevation view of two "ganged" valve assemblies.

An advantage of the new valve assembly 10 is that it can be "ganged" very easily with other assemblies 10. FIG. 7 shows such an arrangement. In that arrangement, there are first and second valve blocks 25a and 25b, respectively. Each such block 25a, 25b has its own outlet passage 33a, 33b as described above. And each such passage 33 has a first end 35 and a second end 37.

In the ganged arrangement, the second end 37 of the first outlet passage 33a and the first end 35 of the second outlet passage 33b are connected together by tubing 71. And the first end 35 of the first outlet passage 33a and the second end 37 of the second outlet passage 33b are connected together by a curvilinear tube 19 similar to that shown in FIG. 3.

Figure 10:
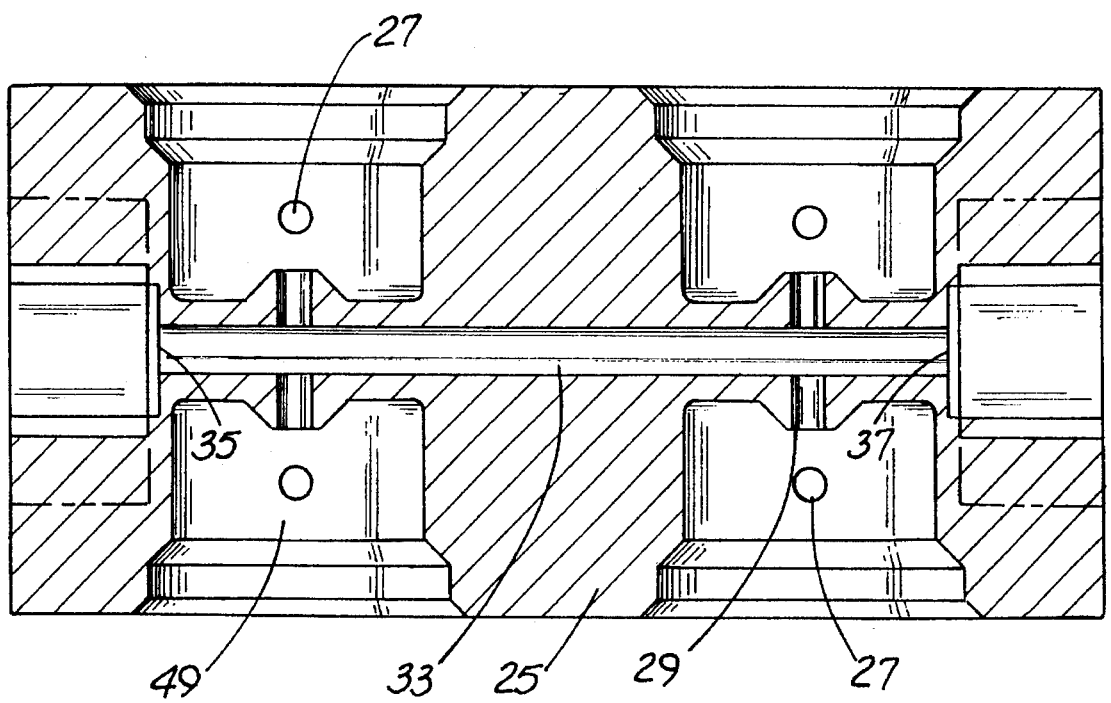
FIG. 10 is a cross-sectional elevation view of the valve block of FIG. 8 taken along the viewing plane 10—10 thereof. Certain surfaces are shown in dashed outline.
Figure 8:
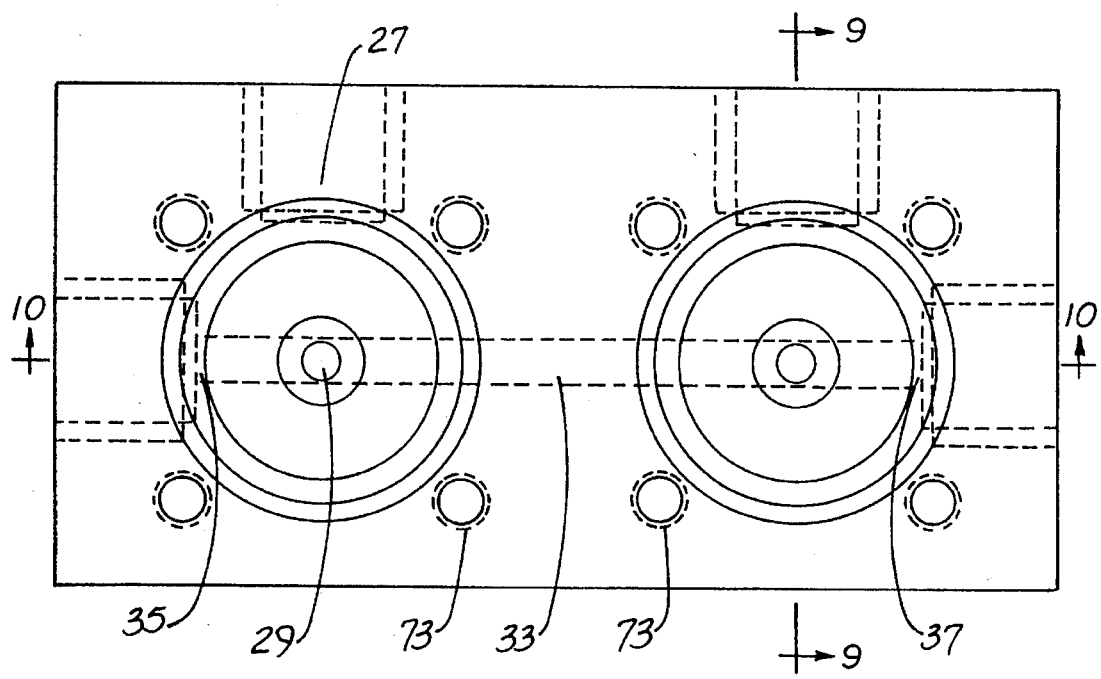
FIG. 8 is a top plan view of the valve block used in the assembly and taken along the viewing plane 8—8 of FIG. 4. Certain surfaces are shown in dashed outline.
Figure 9:
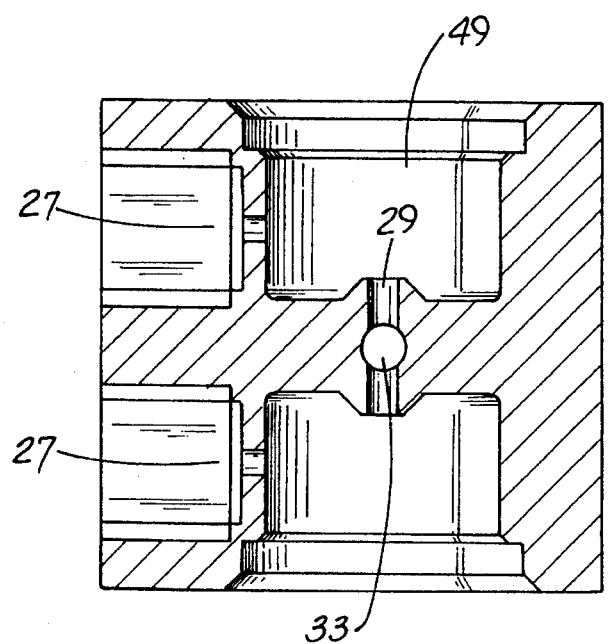
FIG. 9 is a cross-sectional elevation view of the valve block of FIG. 8 taken along the viewing plane 9—9 thereof. Certain surfaces are shown in dashed outline.

FIGS. 8, 9 and 10 show structural details of the valve block 25 including the relative locations of the inlet passages 27, the annular cavities 49, the intermediate flow passages 29 and the outlet passage 33. The tapped holes 73 accept fasteners holding the solenoid valves 39 and the block 25 to one another.

While the principles of the invention have been shown and described in connection with specific embodiments, it is to be understood clearly that such embodiments are exemplary and are not limiting.

What is claimed:

1. In a valve assembly for controlling flow of fluid and having a valve block with (a) at least two inlet passages, and (b) an outlet passage and wherein the assembly has two flow control valves, each for connecting a separate one of said inlet passages to the outlet passage, the improvement wherein:

each valve has a primary valving surface;

each of the two inlet passages is selectively placed in flow communication with the outlet passage by positioning a said primary valving surface; and when a said primary valving surface is positioned to place an inlet passage in flow communication with the outlet passage, the outlet passage carries fluid bi-directionally.

2. The assembly of claim 1 wherein:

the outlet passage has a first end and a second end; and the ends are coupled in flow communication with one another by a curvilinear tube.

3. The assembly of claim 2 wherein:

the tube includes a connector about midway between the ends;

the connector is in flow communication with a fluid analyzing device; and the assembly is a fluid sampling valve.

4. The assembly of claim 2 wherein:

the curvilinear tube has at least one bend of about 180° which is formed along a substantially constant radius of curvature.

5. The assembly of claim 1 wherein:

the block includes at least two intermediate flow passages; and the outlet passage is in flow communication with the intermediate flow passages; and each intermediate flow passage and the outlet passage define a "T" connection.

6. The assembly of claim 5 wherein:

the intermediate flow passages comprise a first intermediate passage and a second intermediate passage;

fluid flow in the first intermediate passage is in a first direction;

fluid flow in the second intermediate passage is in a second direction; and the outlet passage and the first and second intermediate passages join at a common point.

7. The assembly of claim 6 wherein:

the first direction and the second direction are about 180° from one another.

8. The assembly of claim 7 wherein the intermediate flow passages are coaxial.

9. The assembly of claim 8 wherein:

the flow control valves are solenoid-actuated; and the valves move in opposite directions when actuated.

10. The assembly of claim 1 wherein:

the assembly includes a corresponding separate drain passage for each inlet passage;

the primary valving surface abuts a valve face when the valve is closed;

each inlet passage contains pressurized fluid; and the pressurized fluid urges the valving surface toward the valve face when the valve is closed.

11. The assembly of claim 10 wherein pressurized fluid is diverted to the corresponding separate drain passage when the valve is closed.

12. The assembly of claim 11 wherein pressurized fluid is diverted to a drain passage when the valve is closed.

13. An improved manifolded sampling valve assembly for sampling fluid and including:

a valve block having two inlet passages and first and second intermediate flow passages;

a pair of flow control valves, each valve selectively placing a separate inlet passage in flow communication with a separate intermediate flow passage;

and wherein:

flowing fluid is in the first intermediate flow passage; and fluid flows bi-directionally away from the first intermediate flow passage.

14. The valve assembly of claim 13 wherein:

the valve block is a first valve block including a first outlet passage having a first end;

the assembly includes a second valve block having a second outlet passage with a second end;

the first end of the first outlet passage and the second end of the second outlet passage are connected together by tubing having at least one bend of about 180° which is formed along a substantially constant radius of curvature.

15. The valve assembly of claim 14 wherein:

the second valve block has (a) two inlet passages, (b) two intermediate flow passages, and (c) a pair of flow control valves, each valve selectively placing a separate inlet passage in the second valve block in flow communication with a separate intermediate flow passage in the second valve block;

the intermediate flow passages of the second valve block are in flow communication with an outlet passage; and the outlet passage carries fluid bi-directionally.

16. The assembly of claim 15 wherein:

the tube two bends, each of about 180° and each formed along a substantially constant radius of curvature.

17. In a valve assembly for controlling flow of fluid and having a valve block with (a) at least two inlet passages, and (b) an outlet passage and wherein the assembly has a separate flow control valve for connecting each inlet passage to the outlet passage, the improvement wherein:

each valve has a primary valving surface;

each of the two inlet passages is selectively placed in flow communication with the outlet passage by positioning a said primary valving surface;

the assembly includes a drain passage for each inlet passage;

each of the primary valving surfaces abuts a separate valve face when the valve is closed;

each inlet passage contains pressurized fluid; and the pressurized fluid urges the valving surface toward the valve face when the valve is closed.

\* \* \* \* \*